(12) United States Patent
Pachot

(10) Patent No.: US 7,622,249 B2
(45) Date of Patent: Nov. 24, 2009

(54) METHOD FOR DIAGNOSING AND/OR PREDICTING OF A SEPTIC SYNDROME

(75) Inventor: Alexandre Pachot, Quincieux (FR)

(73) Assignee: Biomerieux, Marcy l'Etoile (FR)

( * ) Notice: Subject to any disclaimer, the term of this patent is extended or adjusted under 35 U.S.C. 154(b) by 134 days.

(21) Appl. No.: 10/559,292

(22) PCT Filed: Jun. 2, 2004

(86) PCT No.: PCT/FR2004/050210

§ 371 (c)(1),
(2), (4) Date: Dec. 16, 2005

(87) PCT Pub. No.: WO2004/108957

PCT Pub. Date: Dec. 16, 2004

(65) Prior Publication Data

US 2006/0127912 A1 Jun. 15, 2006

(30) Foreign Application Priority Data

Jun. 3, 2003 (FR) ................................. 03 06660

(51) Int. Cl.
C12Q 1/68 (2006.01)
C12P 19/34 (2006.01)
G01N 33/53 (2006.01)
C07H 21/04 (2006.01)
C07K 14/00 (2006.01)

(52) U.S. Cl. ........................ 435/6; 435/7.1; 435/91.2; 435/91.51; 536/23.5; 530/350

(58) Field of Classification Search ........................ None
See application file for complete search history.

(56) References Cited

U.S. PATENT DOCUMENTS

| | | | |
|---|---|---|---|
| 4,672,040 A | 6/1987 | Josephson | |
| 4,683,195 A | 7/1987 | Mullis et al. | |
| 4,683,202 A | 7/1987 | Mullis | |
| 4,800,159 A | 1/1989 | Mullis et al. | |
| 4,981,783 A | 1/1991 | Augenlicht | |
| 5,234,809 A | 8/1993 | Boom et al. | |
| 5,399,491 A | 3/1995 | Kacian et al. | |
| 5,445,934 A | 8/1995 | Fodor et al. | |
| 5,700,637 A | 12/1997 | Southern | |
| 5,744,305 A | 4/1998 | Fodor et al. | |
| 5,750,338 A | 5/1998 | Collins et al. | |
| 5,807,522 A | 9/1998 | Brown et al. | |
| 6,303,321 B1 | 10/2001 | Tracey et al. | |
| 2005/0037344 A1* | 2/2005 | Stuhlmuller et al. ............ 435/6 |

FOREIGN PATENT DOCUMENTS

| | | |
|---|---|---|
| EP | 0 201 184 A2 | 12/1986 |
| EP | 1 310 567 A2 | 5/2003 |
| FR | 2 780 059 | 12/1999 |
| WO | WO 90/01069 | 2/1990 |
| WO | WO 90/06995 | 6/1990 |
| WO | WO 91/02818 | 3/1991 |
| WO | WO 91/19812 | 12/1991 |
| WO | WO 94/12670 | 6/1994 |
| WO | WO 95/08000 | 3/1995 |
| WO | WO 97/45202 | 12/1997 |
| WO | WO 99/15321 | 4/1999 |
| WO | WO 99/35500 | 7/1999 |
| WO | WO 99/53304 | 10/1999 |
| WO | WO 00/05338 | 2/2000 |
| WO | WO 2004/005539 A1 | 1/2004 |

OTHER PUBLICATIONS

Zanotti, S. et al. Cytokine modulation in sepsis and septic shock. Expert opinion on investigational drugs. 11(8):1061-1075 (Aug. 2002).*
Hultgren, O.H. et al. Microbes and Infection 6:529-535 (Mar. 31, 2004).*
Szabo, S.J. et al. Science 295:338-342 (Jan. 11, 2002).*
Thijs et al., "Time course of cytokine levels in sepsis," Intensive Care Med, 21: S258-S263, 1995.
Casey et al., "Plasma Cytokine and Endotoxin Lewis Correlate with Survival in Patients with the Sepsis Syndrome," Ann Intern Medicine, vol. 119, Issue 8, pp. 771-778, 1993.
Van der Poll et al., "Antiinflammatory Cytokine Responses during Clinical Sepsis and Experimental Endotoxemia: Sequential Measurements of Plasma Soluble Interleukin (IL)-1 Receptor Type II, IL-10, and IL-13," The Journal of Infectious Diseases, 1997, 175:118-122, 1997.
Wang et al, "HMG-1 as a Late Mediator of Endotoxin Lethality in Mice," Science, vol. 285, pp. 248-251, 1999.
Boom et al., "Rapid and Simple Method for Purification of Nucleic Acids," Journal of Clinical Microbiology, vol. 28, No. 3, pp. 495-503, 1990.
Levison et al., "New approaches to the isolation of DNA by ion-exchange chromatography," Journal of Chromatography, 827, p. 337-344, 1998.
Kricka et al., "Nucleic Acid Detection Technologies—Labels, Strategies, and Formats," Clinical Chemistry, No. 45:4, pp. 453-458, 1999.

(Continued)

Primary Examiner—Diana B Johannsen
(74) Attorney, Agent, or Firm—Oliff & Berridge, PLC

(57) ABSTRACT

The present invention relates to a method for diagnosing and/or predicting a septic syndrome, wherein:
a. a biological sample from the patient is made available and biological material is extracted from the biological sample
b. at least four specific reagents which are selected from the following specific reagents are made available: reagent which is specific for the target gene IL-10, reagent which is specific for the target gene TGFβ, reagent which is specific for the target gene HMG1, reagent which is specific for the target gene T-bet, reagent which is specific for the target gene IL-1β, reagent which is specific for the target gene TNFα and reagent which is specific for the target gene GATA-3
c. the expression of at least four target genes selected from: IL-10, TGFβ, HMG1, T-bet, IL-1β, TNFα and GATA-3 is determined.

The present invention also relates to a kit for diagnosing and/or predicting a septic syndrome.

4 Claims, 1 Drawing Sheet

OTHER PUBLICATIONS

Keller et al., DNA Probes, 2nd Ed., Stockton Press, sections 5 and 6, pp. 173-249, 1993.

Holland et al., "Detection of specific polymerase chain reaction product by utilizing the 5'→3' exonuclease activity of *Thermus aquaticus* DNA polymerase," Proc. Nat. Acad. Sci., vol. 88, pp. 7276-7280. 1991.

Chee et al., "Accessing Genetic Information with High-Density DNA arrays," Science, vol. 274, No. 5287, pp. 610-614 1996.

Pease et al., "Light-generated oligonucleotide arrays for rapid DNA sequence analysis", Proc. Natl. Acad. Sci. USA, vol. 91, pp. 5022-5026, 1994.

Ramsay, "DNA Chips: State-of-the art" Nature Biotechnology, vol. 16, pp. 40-44; 1998.

Cheng et al., "Microchip-based Devices for Molecular Diagnosis of Genetic Diseases," Molecular Diagnosis, vol. 1, No. 3, pp. 183-200, 1996.

Livache et al., "Preparation of a DNA matrix via an electrochemically directed copolymerization of pyrrole and oligonucleotides bearing a pyrrole group," Nucleic Acids Research, vol. 22 No. 15, pp. 2915-2921, 1994.

Cheng et al., "Preparation and hybridization analysis of DNA/RNA from *E. coli* on microfabricated bioelectronic chips," Nature Biotechnology, vol. 16 pp. 541-546, 1998.

F. Ginot, "Oligonucleotide Micro-Arrays for Identification of Unknown Mutations: How Far From Reality?" Human Mutation, No. 10, pp. 1-10, 1997.

Bustin, "Quantification of mRNA using real-time reverse transcription PCR (RT-PCR): trends and problems," Journal of Molecular Endocrinology, vol. 29, pp. 23-39, 2002.

Giulietti et al., "An Overview of Real-Time Quantitative PCR: Applications to Quantify Cytokine Gene Expression," Methods, vol. 25, 2001, pp. 386-401.

Bone et al., "Definitions for Sepsis and Organ Failure and Guidelines for the Use of Innovative Therapies in Sepsis," The ACCP/SCCM Consensus Conference Committee, American College of Chest Physicians/Society of Critical Care Medicine, *Chest 101*, vol. 6; 1992, pp. 1644-1655.

Stuhlmüller et al., "Identification of Known and Novel Genes in Activated Monocytes from Patients with Rheumatoid Arthritis," Arthritis and Rheumatism, vol. 43, No. 4, Apr. 2000, pp. 775-790.

Berner et al., "Plasma Levels and Gene Expression of Granulocyte Colony-Stimulating Factor, Tumor Necrosis Factor-α, Interleukin (IL)-1β, IL-6, IL.8, and Soluble Intercellular Adhesion Molecule-1 in Neonatal Early Onset Sepsis," Pediatric Research, vol. 44, No. 4, 1998, pp. 469-477.

Lee, "Proteomics: a technology-driven and technology-limited discovery science," Trends in Biotechnology, vol. 19, No. 6, Jun. 1, 2001, pp. 217-222.

\* cited by examiner

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: primer

<400> SEQUENCE: 1
gcggacaagg cccgtta                                                17

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
agaggaagaa ggccgaagga                                             20
```

METHOD FOR DIAGNOSING AND/OR PREDICTING OF A SEPTIC SYNDROME

The present invention relates to a method for diagnosing and/or predicting a septic syndrome. The invention also relates to a kit for diagnosing and/or predicting a septic syndrome.

The septic syndrome, which is a systemic response to infection, represents one of the primary causes of death in intensive care units. It can result from a bacterial, viral, mycotic or parasitic infection. Within this septic syndrome, a distinction is made, in an ascending order of seriousness, between sepsis, severe sepsis and septic shock. Thus, in 1992, a group of experts proposed criteria for defining these three clinical syndromes (R. C. Bone et al, The ACCP/SCCM Consensus Conference Committee. American College of Chest Physicians/Society of Critical Care Medicine. *Chest* 101 (6): 1644-1655, 1992):

thus, sepsis is a systemic inflammatory response linked to an infection, a severe sepsis is a sepsis which is accompanied by the malfunction of at least one organ, septic shock is a severe sepsis which is associated with persistent hypotension and can be characterized by:
the presence of an identified infectious site,
a generalized inflammatory response which is manifested by at least two of the following signs: a) a temperature higher than 38° C. or lower than 36° C., b) heart rate higher than 90 beats per minute, c) respiratory rate higher than 20 respirations per minute, d) number of leukocytes greater than 12 000/mm$^3$ or less than 4000/mm$^3$,
persistent hypotension despite adequate refilling and treatment with vasopressors.

Generally speaking, the signs of a sepsis, of a severe sepsis and of a septic shock are similar to each other and the difference between these 3 situations principally resides in the magnitude of the disturbance of all the vital functions. During a septic shock, it is mainly a fall in arterial pressure, tachycardia, polypnea, blotchiness of the skin, hypothermia or hyperthermia and shivering which are observed. These signs are also accompanied by a malfunction of "target" organs, with a deterioration in the function of organs at a distance from the focus of infection (with kidneys, lungs, central nervous system, digestive apparatus and hematological system being the most frequently affected) being expressed as oliguria (<0.5 ml/kg/h), renal insufficiency, hypoxemia, thrombopenia, agitation and confusion.

The development of a septic syndrome from the stage of sepsis towards a stage of severe sepsis and then septic shock is not unconditional since approximately 64% of septic patients develop severe sepsis and 23% of patients with severe sepsis progress to septic shock. Before this final stage of septic shock is reached, the patient should be prescribed treatments designed to interrupt and reverse the physiopathological process. Thus, it is necessary to restore a satisfactory hemodynamic state and to ensure efficient ventilation. It is also necessary to simultaneously pursue symptomatic treatment of the shock and an antibiotic treatment which is matched as soon as possible to the bacteriological findings.

It thus appears that, while some patients who are developing a septic syndrome, in particular a septic shock, can be restored by means of standard medical care, such as a broad-spectrum antibiotic treatment which is put in place before the results of the bacteriological analyses indicating the source of the infection, other patients, who are developing a much more serious septic syndrome, require the putting in place of powerful treatments such as activated protein C. Over and above the very high cost, this type of therapy exposes patients to the risk of very substantial side effects (coagulatory disorders, etc.). It is therefore very important to efficiently target patients who are capable of benefiting from such a treatment.

For this reason, early diagnosis of a septic syndrome is essential and makes it possible to propose a treatment which is suited to the patient. Furthermore, predicting the septic syndrome and, in particular, a septic shock is vital for proposing a suitable treatment for each patient and distinguishing, at as early a stage as possible, patients who are presenting a poor-prognosis septic syndrome, and who require powerful therapy, from good-prognosis patients.

At present, the diagnosis and prognosis of a septic syndrome, in particular of septic shock, are principally based on the number of visceral failures, the response to the symptomatic treatment, the accessibility, to medical and/or surgical treatment, of the initial focus of infection and of any possible metastatic foci.

However, this suffers from the drawback of only being applicable at an advanced stage of the septic syndrome, in particular of septic shock, thus reducing the chances of the patients surviving.

The diagnosis and prognosis of a septic syndrome can also be based on detecting certain soluble factors or proteins, such as the cytokines, which are involved in the syndrome. Mention may be made, in particular, of the publication by Thijs & Hack (Intensive Care Med, 1995, 21: S258-S263), which gives a list of the plasma concentrations of certain cytokines such as TNF, IL-1b, IL-6 and IL-8 during sepsis. Thus, assaying cytokines which are involved in the development of a septic syndrome can be a means for diagnosing and predicting a septic syndrome. Thus, these authors reported a positive correlation between the plasma content of IL-1 (interleukin-1) and a poor-prognosis septic syndrome (Thijs & Hack, Intensive Care Med 21: S258-263, 1995). However, other authors have not found any correlation between IL-1 and a poor-prognosis septic syndrome, suggesting that this factor is very variable. In addition, high measured values of TNF (tumor necrosis factor) have also been associated with a poor prognosis (Casey et al., Ann Intern Med. 1993, 119:771-778). TNF-α and then 11-1β are the first two proinflammatory cytokines which are released by the monocytes after the onset of a septic state.

Other authors have shown that the plasma content of IL-10 (interleukin-10) is higher in patients who are developing a poor-prognosis sepsis whereas it falls significantly in patients who are presenting a good-prognosis sepsis and is not detectable in healthy patients (Van der Poll, J. Infect. Dis. 175:118-122, 1997). IL-10 is a very important anti-inflammatory cytokine which, by its ability to inhibit the production of TNF-α and IL-1β, is involved in establishing a state of immunoparalysis. However, since this increase in the content of IL-10 is only detectable in 80% of patients in septic shock, the sole detection of this factor remains insufficient for predicting the development of the septic shock.

Mention may also be made of the U.S. Pat. No. 6,303,321 which describes a method for predicting the severity of a septic syndrome, which method comprises measuring the serum concentration of HMG1 (high mobility group 1 protein) using an immunoblotting technique. Contrary to TNF-α and IL-1β, HMG1 is described as being a late proinflammatory mediator of septic syndromes. A high concentration of HMG1 is correlated with a poor prognosis, with no HMG1 serum concentration being detected in healthy patients. On the other hand, posttranscriptional regulation of the HMG1 gene has been described in mice, with this suggesting that the expression of this gene should only be analyzed at the protein level (Wang et al, Science, 1999, Vol. 285, p. 248-251).

However, it is important to note that, at the present time, no cytokine is recognized by common consent as being a tool for diagnosing or predicting a septic syndrome. Furthermore, assaying cytokines in the plasma is based on an antigen/antibody reaction which can be distorted by the existence of crossreactions with other nonspecific antigens of the cytokines or by the presence of cytokines which are complexed with a soluble receptor in plasma.

The present invention intends to resolve the drawbacks of the prior art by presenting a novel, reliable tool for diagnosing and/or predicting a septic syndrome, such as, in particular, a septic shock.

Surprisingly, the inventors have demonstrated that the diagnosis and/or prognosis of a septic syndrome can be determined by studying a panel of genes selected from IL-10, TGFβ, HMG1, T-bet (T cell-specific T-box transcription factor, T bet), IL-1β, GATA-3 (GATA-binding protein 3) and TNF-α. Furthermore, analyzing the expression of several of these genes in a single step makes it possible to obtain a tool which is very effective for predicting and/or diagnosing a septic syndrome.

Before proceeding further, the following definitions are given for improving the comprehension of the invention.

A septic syndrome is understood as being a systemic response to an infection. This septic syndrome can be at a stage of sepsis, severe sepsis or septic shock. The septic syndrome is preferably a septic shock.

A biological sample is understood as being any material which is derived from the patient, which is capable of containing a biological material which enables the expression of a gene to be detected and which can, in particular, be a sample of blood, of serum, of saliva, of tissue or of circulating cells from the patient. This biological sample is obtained by any type of withdrawal known to the skilled person, such as, in particular, taking a blood sample.

Biological material is understood as being any material, such as, in particular, a nucleic acid or a protein, which enables the expression of a gene to be detected. The nucleic acid can, in particular, be an RNA (ribonucleic acid) such as an mRNA (messenger RNA). According to a preferred embodiment of the invention, the biological material is a nucleic acid, even more preferably an mRNA (messenger RNA).

The extraction of the biological material from the biological sample in step a) can be effected using any protocols for extracting nucleic acids or proteins which are well known to the skilled person.

As a rough guide, nucleic acids can be extracted, in particular, by:
  a step of lyzing the cells which are present in the biological sample in order to release the nucleic acids which are present in the protein and/or lipid envelopes of the microorganisms (as cell debris which interfere with the subsequent reactions). By way of example, it is possible to use the lysis methods which are described in the applicant's patent applications:
    WO-A-00/05338 on magnetic and mechanical mixed lysis,
    WO-A-99/53304 on electric lysis, and
    WO-A-99/15321 on mechanical lysis.
  The skilled person will be able to use other well known lysis methods such as thermal or osmotic shock or chemical lysis using chaotropic agents such as guanidium (U.S. Pat. No. 5,234,809).
  a step of purification, enabling the nucleic acids to be separated from the other cell constituents which are released in the lysis step. This step generally enables the nucleic acids to be concentrated. By way of example, it is possible to use magnetic particles which may be coated, by adsorption or covalence, with oligonucleotides (in this regard, see the U.S. Pat. No. 4,672,040 and U.S. Pat. No. 5,750,338) and in this way purify the nucleic acids, which have become attached to these magnetic particles, by means of a washing step. This step of purifying the nucleic acids is particularly advantageous if there is a need to subsequently amplify said nucleic acids. A particularly advantageous embodiment of these magnetic particles is described in the patent applications filed by the applicant under the following references: WO-A-97/45202 and WO-A-99/35500. Another advantageous example of a method for purifying the nucleic acids is that of using silica either in the form of a column or in the form of inert (Boom R. et al., J. Clin. Microbiol., 1990, No. 28(3), p. 495-503) or magnetic (Merck: MagPrep® Silica, Promega: Magne-Sil™ Paramagnetic particles) particles. Other very widely used methods are based on ion exchange resins in columns or in paramagnetic particle format (Whatman: DEAE-Magarose) (Levison P R et al., J. Chromatography, 1998, p. 337-344). Another method which is very relevant but which is not exclusive for the invention is that of adsorption on a metallic oxide support (Xtrana company: Xtra-Bind™ matrix).

A specific reagent is understood as being a reagent which reacts with the biological material for the purpose of directly or indirectly demonstrating the expression of a target gene, which can be determined either by analyzing the mRNA which is derived from this gene or by analyzing the protein which is encoded by this gene.

As a rough guide, when there is a need to determine the expression of a target gene by analyzing the protein encoded by this gene, this specific reagent then comprises at least one antibody which is specific for the protein which is encoded by this target gene. As a rough guide, when there is a need to determine the expression of a target gene by analyzing the mRNA transcripts from this gene, this specific reagent then comprises at least one amplification primer which is specific for the DNA which is complementary to this mRNA (this is then referred to as an amplification primer which is specific for a target gene). The DNA which is complementary to an mRNA can be obtained using a protocol which is well known to the skilled person. As a rough guide, the total RNA (comprising the ribosomal RNA, the transfer RNA and the mRNA) is extracted from the biological sample in step a) of the method according to the invention. A reverse transcription reaction is then carried out using a reverse transcriptase enzyme which enables a complementary fragment of DNA to be obtained from a fragment of RNA. Implementing this step is well known to the skilled person. When there is a need, more specifically, to only obtain the DNA which is complementary to the messenger RNA, this enzymic step is then carried out in the presence of nucleotide fragments which consist solely of thymine bases (polyT), which hybridize, as a result of complementarity, with the polyA sequences of the different mRNAs in order to form a polyT-polyA complex which then serves as a starting point for the reverse transcription reactions which are implemented using the reverse transcriptase enzyme. This then results in different DNAs which are complementary to the different messenger RNAs which were initially present in the biological sample. In the remainder of the account, cDNA is understood as meaning a DNA which is complementary to a messenger RNA.

An amplification primer is understood as being a nucleotide fragment which comprises from 5 to 100 nucleotide motifs, preferably from 15 to 25 nucleotide motifs, and which possesses a specificity of hybridization under conditions which are determined for initiating an enzymic polymerization, for example in an enzymic amplification reaction.

An enzymic amplification reaction is understood as being a process which generates, by the action of at least one enzyme, multiple copies of a target nucleotide fragment using specific amplification primers. Such amplification reactions are well known to the skilled person and the following techniques may be mentioned, in particular:

PCR (polymerase chain reaction), as described in the U.S. Pat. Nos. 4,683,195, 4,683,202 and 4,800,159, LCR (ligase chain reaction), which is explained, for example, in the patent application EP-A-0 201 184, RCR (repair chain reaction), which is described in the patent application WO-A-90/01069, 3SR (self-sustained sequence replication) together with the patent application WO-A-90/06995, NASBA (nucleic acid sequence-based amplification), together with the patent application WO-A-91/02818, and TMA (transcription-mediated amplification) together with the U.S. Pat. No. 5,399,491.

The term amplicons is then used for designating the polynucleotides which are generated by an enzymic amplification technique. Preferably, when the enzymic amplification is a PCR, the specific reagent comprises at least 2 specific amplification primers for the purpose of amplifying a particular region of the DNA which is complementary to the mRNA which is derived from the target gene. When the enzymic amplification is a PCR which is implemented after reverse transcription reaction, this is then referred to as RT-PCR.

A hybridization probe is understood as being a nucleotide fragment which comprises from 5 to 100 nucleotide motifs, in particular from 6 to 35 nucleotide motifs, and which possesses a hybridization specificity, under determined conditions, for forming a hybridization complex with a target nucleotide fragment. In the present invention, the target nucleotide fragment can be a nucleotide sequence included in a messenger RNA or a nucleotide sequence included in a complementary DNA which is obtained by reverse-transcribing said messenger RNA.

Hybridization is understood as being the process during which, under appropriate conditions, two nucleotide fragments, such as, for example, a hybridization probe and a target nucleotide fragment, which have sequences which are sufficiently complementary are able to form a double strand by means of stable and specific hydrogen bonds. A nucleotide fragment which is "able to hybridize" with a polynucleotide is a fragment which is able to hybridize with said polynucleotide under hybridization conditions which can be determined in each case in a known manner. The hybridization conditions are determined by the stringency, that is to say the rigor of the operational conditions. The specificity of the hybridization is directly proportional to the stringency under which the hybridization is effected. The stringency is defined, in particular, in accordance with the base composition of a probe/target duplex as well as by the degree of mispairing between two nucleic acids. The stringency can also be a function of the parameters of the reaction, such as the concentration and type of the ionic species which are present in the hybridization solution, the nature and concentration of denaturing agents and/or the hybridization temperature. The stringency of the conditions under which a hybridization reaction is to be carried out will mainly depend on the hybridization probes which are employed. All these facts are well known, and the appropriate conditions can be determined by the skilled person. In general, depending on the length of the hybridization probes employed, the temperature for the hybridization reaction is between 20 and 70° C., in particular between 35 and 65° C., in a saline solution having a concentration of from about 0.5 to 1 M. A step of detecting the hybridization reaction is then carried out.

Detection is understood as being either direct detection by means of a physical method or a detection method which uses a label. A large number of detection methods for detecting nucleic acids exist. [See, for example, Kricka et al., Clinical Chemistry, 1999, No. 45(4), p. 453-458 or Keller G. H. et al., DNA Probes, 2nd Ed., Stockton Press, 1993, sections 5 and 6, p. 173-249]. A label is understood as being a tracer which is able to engender a signal. A non-limiting list of these tracers comprises the enzymes, such as horseradish peroxidase, alkaline phosphatase, betagalactosidase, and glucose 6-phosphate dehydrogenase, which produce a signal which can be detected, for example, by colorimetry, fluorescence or luminescence; chromophores such as fluorescent, luminescent or dyeing compounds, groups having an electron density which can be detected by electron microscopy or by their electrical properties such as conductivity, by the methods of amperometry or voltametry, or by impedance measurements, groups which can be detected by optical methods such as diffraction, surface plasmon resonance or contact angle variation, or by means of physical methods, such as atomic force spectroscopy, tunnel effect, etc., radioactive molecules such as $^{32}$P, $^{35}$S and $^{125}$I. Thus, the polynucleotide can be labeled during the enzymic amplification step by, for example, using a labeled nucleotide triphosphate for the amplification reaction. The labeled nucleotide will be a deoxyribonucleotide in the amplification systems, such as PCR, which generate a DNA, or a ribonucleotide in the amplification techniques, such as TMA or NASBA techniques, which generate an RNA. The polynucleotide can also be labeled after the amplification step, for example by hybridizing on a labeled probe using the sandwich hybridization technique described in the document WO-A-91/19812.

Another particularly preferred method of labeling nucleic acids is described in the applicant's application FR-A-2 780 059. Another preferred method of detection uses the 5'-3' exonuclease activity of a polymerase, as described by Holland P. M., PNAS (1991) p 7276-7280.

Systems for amplifying the signal can be used as described in the document WO-A-95/08000 and, in this case, the preliminary enzyme amplification reaction may not be necessary.

In the context of the present invention, the hybridization probe can be a probe which is termed a capture probe. In this case, the target nucleotide fragment can have been previously labeled with a label. The capture probe is immobilized, or immobilizable, on a solid support using any appropriate means, that is to say directly or indirectly, for example by covalence or adsorption. A hybridization reaction is then carried out between said detection probe and the labeled target nucleotide fragment.

The hybridization probe can also be a probe which is termed a detection probe. In this case, the hybridization probe can be labeled with a label. A hybridization reaction is then carried out between said capture probe and the target nucleotide fragment.

Whether a capture probe or a detection probe is used, the hybridization reaction can be carried out on a solid support, which includes any materials on which a nucleic acid can be immobilized. Synthetic materials or natural materials, which may possibly have been modified chemically, can be used as the solid support, in particular polysaccharides such as cellulose-based materials, for example paper, cellulose derivatives such as cellulose acetate and nitrocellulose or dextran, polymers, copolymers, in particular based on monomers of the styrene type, natural fibers such as cotton and synthetic fibers such as nylon, mineral materials such as silicon, quartz, glasses and ceramics, latexes, magnetic particles, metallic derivatives, gels, etc. The solid support can be in the form of a microtitration plate, of a membrane as described in the application WO-A-94/12670, of a particle or of a biochip. A biochip is understood as being a solid support of reduced size on which a multiplicity of capture probes are fixed at predetermined positions. The biochip, more precisely the DNA chip, concept dates from the beginning of the 1990s. Nowadays, this concept has widened since protein chips are beginning to be developed. It is based on a multidisciplinary technology which integrates microelectronics, nucleic acid chemistry, image analysis and computing. The working principle is based on a fundamental of molecular biology: the phenomenon of hybridization, that is to say the pairing, as a result of complementarity, of the bases of two DNA and/or RNA sequences. The biochip method is based on using capture probes which are fixed on a solid support and on which a sample of target nucleotide fragments which are labeled directly or indirectly with fluorochromes are caused to act. The capture probes are located specifically on the support or chip and each hybridization provides specific information in relation to the target nucleotide fragment. The items of information which are obtained are cumulative and make it possible, for example, to quantify the level of expression of a gene or of several target genes. In order to analyze the expression of a target gene, it is then possible to make a biochip which carries a very large number of probes which correspond to all or part of the target gene which has been transcribed into mRNA. The DNAs, for example, which are complementary to the mRNAs which are derived from the target gene(s) which it is desired to analyze are then hybridized. After hybridization, the support or chip is washed and read, for example using a scanner, and the analysis of the fluorescence is processed using a computer. As a rough guide, mention may be made of the DNA chips which have been developed by the company Affymetrix ("Accessing Genetic Information with High-Density DNA arrays", M. Chee et al., Science, 1996, 274, 610-614; "Light-generated oligonucleotide arrays for rapid DNA sequence analysis", A. Caviani Pease et al., Proc. Natl. Acad. Sci. USA, 1994, 91, 5022-5026) for molecular diagnoses. In this technology, the capture probes are generally of reduced size, being around twenty nucleotides. Other examples of biochips are given in the publications by G. Ramsay, Nature Biotechnology, 1998, No. 16, p. 40-44; F. Ginot, Human Mutation, 1997, No. 10, p. 1-10; J. Cheng et al, Molecular diagnosis, 1996, No. 1(3), p. 183-200; T. Livache et al, Nucleic Acids Research, 1994, No. 22(15), p. 2915-2921; J. Cheng et al, Nature Biotechnology, 1998, No. 16, p. 541-546 or in the U.S. Pat. Nos. 4,981,783, 5,700,637, 5,445,934, 5,744,305 and 5,807,522. The main characteristic of the solid support should be that of preserving the hybridization characteristics of the capture probes with regard to the target nucleotide fragments while at the same time generating a background noise which is minimum for the detection method.

In the present invention, the determination of the expression of target genes can be analyzed by the expression of the mRNAs which are transcribed at a given moment. In this case, the biological material is a nucleic acid and the specific reagent can equally well be an amplification primer or a hybridization probe as previously defined. The expression of a target gene can also be analyzed by the expression of the proteins which are encoded by the target gene. In this case, the biological material is a protein and the specific reagent can be an antibody which is specific for the protein which is encoded by the target gene. As a rough guide, it is possible to determine the expression of a target gene in the following manner:

1) after having extracted the total RNA from a biological sample as defined in step a) of the method according to the invention as previously presented, a step of reverse transcription, as previously described, is carried out in order to obtain the different DNAs (or cDNAs) which are complementary to the different messenger RNAs which were initially present in the biological sample
2) the cDNAs are amplified specifically. In this case, the specific reagent employed comprises at least one amplification primer which is specific for the target gene as previously defined. This step can be carried out, in particular, by means of an amplification reaction of the PCR type or by means of any other amplification technique as previously defined. It is also possible to simultaneously amplify the cDNAs from several target genes: this is then referred to as being a multiplex amplification;
3) the expression of the target gene is determined by quantifying the cDNAs. The cDNAs can be quantified, in particular, by using a quantification range which is obtained by means of an amplification reaction which is taken to saturation. In order to take account of the variability in enzymic efficacy which can be observed in the different steps (reverse transcription, PCR, etc.), it is possible to normalize the expression of the target gene in the different groups of patients by simultaneously determining the expression of what is termed a housekeeping gene, the expression of which is similar in the different groups of patients. Constructing a ratio between the expression of the target gene and the expression of a housekeeping gene thereby corrects any variability between the different experiments. The skilled person will be able to refer, in particular, to the following publications: Bustin SA *Journal of molecular endocrinology*, 2002, 29: 23-39; Giulietti A *Methods*, 2001, 25: 386-401.

It is also possible to determine the expression of a target gene in the following manner:

1) after having extracted the total RNA from a biological sample as defined in step a) of the method according to the invention as previously presented, a step of reverse transcription, as previously described, is carried out in order to obtain the different DNAs (or cDNAs) which are complementary to the different messenger RNAs which were initially present in the biological sample
2) the cDNAs are immobilized on a membrane
3) the expression of the target gene is determined by hybridizing the cDNAs with previously labeled hybridization probes which are specific for the target gene. These hybridization techniques are well known to the skilled person and mention may be made, in particular, of the technique of Northern blotting. This hybridization reaction can be carried out after a step of specifically amplifying the DNAs which are complementary to the messenger RNAs of a target gene when, in particular, the gene is weakly expressed.

The analysis of the expression of a target gene then provides a tool for diagnosing and/or predicting a septic syndrome. It is possible, for example, to analyze the expression of a target gene in a patient the prognosis of whose septic syndrome is unknown and, by comparing with the known mean expression values of the target gene in good-prognosis patients and with the known mean expression values of the target gene in poor-prognosis patients, to determine whether the patient is a good-prognosis patient or a poor-prognosis patient in order to propose a treatment which is appropriate for this patient. It is also possible to simultaneously study the expression of several target genes by, in particular, using a biochip, and the expression of several target genes is then determined, in a single step, that is to say on the basis of one and the same sample and by means of a single analysis (with the aid of repeated assays or by measuring in a single step). The genes of a patient the prognosis of whose septic syndrome is unknown are then analyzed globally and, by comparing with the known mean expression values from one and the same panel of target genes from good-prognosis patients and the known mean expression values from one and the same panel of target genes from poor-prognosis patients, it is then possible to determine whether the patient is a good-prognosis patient or a poor-prognosis patient in order to propose a treatment which is appropriate for this patient.

Thus, the invention relates to a method for diagnosing and/or predicting a septic syndrome, wherein:

a. a biological sample from the patient is made available and biological material is extracted from the biological sample b. at least four specific reagents which are selected from the following specific reagents are made available: reagent which is specific for the target gene IL-10, reagent which is specific for the target gene TGFβ, reagent which is specific for the target gene HMG1, reagent which is specific for the target gene T-bet, reagent which is specific for the target gene IL-1β, reagent which is specific for the target gene TNFα and reagent which is specific for the target gene GATA-3 c. the expression of at least four target genes selected from: IL-10, TGFβ, HMG1, T-bet, IL-1β, TNFα and GATA-3 is determined.

According to a preferred embodiment of the invention, the biological sample is a blood sample. According to a preferred embodiment of the invention, the biological material is a nucleic acid.

According to a preferred embodiment of the invention, the total RNA is extracted from the biological sample.

According to a preferred embodiment of the invention, the reagent which is specific for IL10 comprises at least one amplification primer which is specific for the target gene IL-10, the reagent which is specific for TGFβ comprises at least one amplification primer which is specific for the target gene TGFβ, the reagent which is specific for HMG1 comprises at least one amplification primer which is specific for the target gene HMG1, the reagent which is specific for T-bet comprises at least one amplification primer which is specific for the target gene T-bet, the reagent which is specific for IL-1β comprises at least one amplification primer which is specific for the target gene IL-1β, the reagent which is specific for TNFα comprises at least one amplification primer which is specific for the target gene TNFα and/or the reagent which is specific for GATA 3 comprises at least one amplification primer which is specific for the target gene GATA 3.

According to another embodiment of the invention, the specific reagent according to the invention comprises at least one hybridization probe which is specific for a target gene. Preferably, the reagent which is specific for IL10 comprises at least one hybridization probe which is specific for the target gene IL-10, the reagent which is specific for TGFβ comprises at least one hybridization probe which is specific for the target gene TGFβ, the reagent which is specific for HMG1 comprises at least one hybridization probe which is specific for the target gene HMG1, the reagent which is specific for T-bet comprises at least one hybridization probe which is specific for the target gene T-bet, the reagent which is specific for IL-1β comprises at least one hybridization probe which is specific for the target gene IL-1β, the reagent which is specific for TNFα comprises at least one hybridization probe which is specific for the target gene TNFα and/or the reagent which is specific for GATA 3 comprises at least one hybridization probe which is specific for the target gene GATA 3. This probe can be a detection probe or a capture probe such as, in particular, a capture probe which is immobilized on a biochip.

The invention preferably relates to determining the expression of the target genes by analyzing the expression of the mRNAs.

According to a preferred embodiment of the invention, at least two specific reagents which are selected from the following specific reagents are made available in step b) of the method according to the invention: reagent which is specific for the TGFβ gene and reagent which is specific for the HMG1 gene, and the expression of at least two target genes selected from: TGFβ and HMG1 is determined in step c) of the method according to the invention.

According to a preferred embodiment of the invention, at least three, preferably at least four and even more preferably at least five specific reagents which are selected from the following specific reagents are made available in step b) of the method according to the invention: reagent which is specific for the IL-10 gene, reagent which is specific for the TGFβ gene, reagent which is specific for the HMG1 gene, reagent which is specific for the T-bet gene, reagent which is specific for the IL-1β gene, reagent which is specific for the TNFα gene, and reagent which is specific for the GATA-3 gene, and the expression of at least 3, preferably at least 4, and even more preferably at least 5, genes selected from IL-10, TGFβ, HMG1, T-bet, IL-1β, TNFα and GATA-3 in step c) of the method according to the invention. According to a preferred embodiment of the invention, at least three specific reagents which are selected from the following specific reagents are made available in step b) of the method according to the invention: reagent which is specific for the TGFβ gene, reagent which is specific for the HMG1 gene and reagent which is specific for the IL-1β gene, and the expression of at least three target genes selected from: TGFβ, HMG1 and IL-1β is determined in step c) of the method according to the invention.

According to another preferred embodiment of the invention, at least four specific reagents which are selected from the following specific reagents are made available in step b) of the method according to the invention: reagent which is specific for the TGFβ gene, reagent which is specific for the HMG1 gene, reagent which is specific for the IL-1β gene and reagent which is specific for the IL-10 gene, and the expression of at least four target genes selected from: TGFβ, HMG1, IL-1β and IL-10 is determined in step c) of the method according to the invention.

According to another preferred embodiment of the invention, at least five specific reagents which are selected from the following specific reagents are made available in step b) of the method according to the invention: reagent which is specific for the TGFβ gene, reagent which is specific for the HMG1 gene, reagent which is specific for the IL-1β gene, reagent which is specific for the IL-10 gene and reagent which is specific for the T-bet gene, and the expression of at least five target genes selected from: TGFβ, HMG1, IL-1β, IL-10 and T-bet is determined in step c) of the method according to the invention.

The invention also relates to a method for diagnosing and/or predicting a septic syndrome as previously defined, wherein:

a. a biological sample from the patient, as previously defined, is made available and biological material, as previously defined, is extracted from the biological sample b. at least one reagent which is specific for a gene selected from the following genes: IL-10, T-bet and GATA-3 is made available c. the expression, as previously defined, of at least one target gene selected from: IL-10, T-bet and GATA-3 is determined.

According to a preferred embodiment of the invention, the biological sample is a blood sample.

According to a preferred embodiment of the invention, the biological material is a nucleic acid.

According to a preferred embodiment of the invention, the specific reagent is an amplification primer which is as previously defined and is specific for a gene selected from IL-10, T-bet and GATA 3.

According to another preferred embodiment of the invention, the reagent which is specific for IL-10, T-bet or GATA 3 is a hybridization probe which is as previously defined and is specific, respectively, for the target genes IL-10, T-bet or GATA 3.

The invention also relates to a method for diagnosing and/or predicting a septic syndrome wherein:

a. a biological sample from the patient is made available and the total RNA is extracted from the biological sample b. at least one reagent which is specific for the HMG1 gene is made available c. the expression of the mRNAs from the HMG1 gene is determined.

It will be very obvious that, in this method, the wish is not to detect the expression of the HMG1 gene at the protein level but, instead, solely at the level of the mRNAs. The reagent which is specific for the HMG1 gene is preferably an amplification primer or a hybridization probe as previously defined.

The invention also relates to a kit for diagnosing and/or predicting a septic syndrome, comprising at least four specific reagents which are selected from the following specific reagents: reagent which is specific for the IL-10 gene, reagent which is specific for the TGFβ gene, reagent which is specific for the HMG1 gene, reagent which is specific for the T-bet gene, reagent which is specific for the IL-1β gene, reagent which is specific for the TNFα gene and reagent which is specific for the GATA-3 gene.

According to a preferred embodiment of the invention, the reagent which is specific for IL10 comprises at least one amplification primer which is specific for the target gene IL-10, the reagent which is specific for TGFβ comprises at least one amplification primer which is specific for the target gene TGFβ, the reagent which is specific for HMG1 comprises at least one amplification primer which is specific for the target gene HMG1, the reagent which is specific for T-bet comprises at least one amplification primer which is specific for the target gene T-bet, the reagent which is specific for IL-1β comprises at least one amplification primer which is specific for the target gene IL-1β, the reagent which is specific for TNFα comprises at least one amplification primer which is specific for the target gene TNFα and/or the reagent which is specific for GATA 3 comprises at least one amplification primer which is specific for the target gene GATA 3.

According to another embodiment of the invention, the reagent which is specific for IL10 comprises at least one hybridization probe which is specific for the target gene IL-10, the reagent which is specific for TGFβ comprises at least one hybridization probe which is specific for the target gene TGFβ, the reagent which is specific for HMG1 comprises at least one hybridization probe which is specific for the target gene HMG1, the reagent which is specific for T-bet comprises at least one hybridization probe which is specific for the target gene T-bet, the reagent which is specific for IL-1β comprises at least one hybridization probe which is specific for the target gene IL-1β, the reagent which is specific for TNFα comprises at least one hybridization probe which is specific for the target gene TNFα and/or the reagent which is specific for GATA 3 comprises at least one hybridization probe which is specific for the target gene GATA 3.

The invention also relates to a kit for diagnosing and/or predicting a septic syndrome, comprising at least one specific reagent which is selected from the following specific reagents: reagent which is specific for the IL-10 gene, reagent which is specific for the T-bet gene and reagent which is specific for the GATA-3 gene.

According to a preferred embodiment of the invention, the reagent which is specific for IL10 comprises at least one amplification primer which is specific for the target gene IL-10, the reagent which is specific for T-bet comprises at least one amplification primer which is specific for the target gene T-bet and/or the reagent which is specific for GATA 3 comprises at least one amplification primer which is specific for the target gene GATA 3.

According to another preferred embodiment of the invention, the reagent which is specific for IL10 comprises at least one hybridization probe which is specific for the target gene IL10, the reagent which is specific for T-bet comprises at least one hybridization probe which is specific for the target gene T-bet and/or the reagent which is specific for GATA 3 comprises at least one hybridization probe which is specific for the target gene GATA 3.

The invention also relates to a method for diagnosing and/or predicting a septic syndrome, wherein:

a. a biological sample from the patient is made available and biological material is extracted from the biological sample b. at least two reagents which are specific for at least two target genes selected from: IL-10, TGFβ, HMG1, T-bet, IL-1β, TNFα and GATA-3 are made available c. the expression of at least two target genes selected from: IL-10, TGFβ, HMG1, T-bet, IL-1β, TNFα and GATA-3 is determined in a single step.

According to a preferred embodiment of the invention, the biological sample is a blood sample.

According to a preferred embodiment of the invention, the total RNA is extracted from the biological sample.

According to the invention, the target gene is selected from IL-10, TGFβ, HMG1, T-bet, IL-1β, TNFα and GATA-3.

According to a preferred embodiment of the invention, the reagent which is specific for IL10 comprises at least one amplification primer which is specific for the target gene IL-10, the reagent which is specific for TGFβ comprises at least one amplification primer which is specific for the target gene TGFβ, the reagent which is specific for HMG1 comprises at least one amplification primer which is specific for the target gene HMG1, the reagent which is specific for T-bet comprises at least one amplification primer which is specific for the target gene T-bet, the reagent which is specific for IL-1β comprises at least one amplification primer which is specific for the target gene IL-1β, the reagent which is specific for TNFα comprises at least one amplification primer which is specific for the target gene TNFα and/or the reagent which is specific for GATA 3 comprises at least one amplification primer which is specific for the target gene GATA 3.

According to another embodiment of the invention, the specific reagent according to the invention comprises at least one hybridization probe which is specific for a target gene. Preferably, the reagent which is specific for IL10 comprises at least one hybridization probe which is specific for the target gene IL-10, the reagent which is specific for TGFβ comprises at least one hybridization probe which is specific for the target gene TGFβ, the reagent which is specific for HMG1 comprises at least one hybridization probe which is specific for the target gene HMG1, the reagent which is specific for T-bet comprises at least one hybridization probe which is specific for the target gene T-bet, the reagent which is specific for IL-1β comprises at least one hybridization probe which is specific for the target gene IL-1β, the reagent which is specific for TNFα comprises at least one hybridization probe which is specific for the target gene TNFα and/or the reagent which is specific for GATA 3 comprises at least one hybridization probe which is specific for the target gene GATA 3. This probe can be a detection probe or a capture probe such as, in particular, a capture probe which is immobilized on a biochip.

The invention preferably relates to determining the expression of the target genes by analyzing the expression of the mRNAs.

In step c), the expression of at least two target genes is determined in a single step, that is to say on the basis of one and the same sampling and by means of a single analysis (with the aid of repeated assays or by measuring in one single step). The genes for a patient the prognosis of whose septic syndrome is unknown are then analyzed globally and, by comparing with known mean expression values from one and the same panel of target genes from good-prognosis patients and known mean expression values from one and the same panel of target genes from poor-prognosis patients, it is then possible to determine whether the patient is a good-prognosis patient or a poor-prognosis patient in order to propose a treatment which is appropriate for this patient.

According to a preferred embodiment of the invention, at least three, preferably at least four and even more preferably at least five, specific reagents which are selected from the following specific reagents are made available in step b) of the method according to the invention: reagent which is specific for the IL-10 gene, reagent which is specific for the TGFβ gene, reagent which is specific for the HMG1 gene, reagent which is specific for the T-bet gene, reagent which is specific for the IL-1β gene, reagent which is specific for the TNFα gene and reagent which is specific for the GATA-3 gene, and the expression of at least 3, preferably of at least 4, and even more preferably of at least 5, genes selected from IL-10, TGFβ, HMG1, T-bet, IL-1β, TNFα and GATA-3 is determined in step c) of the method according to the invention.

According to a preferred embodiment of the invention, at least three specific reagents which are selected from the following specific reagents are made available in step b) of the method according to the invention: reagent which is specific for the TGFβ gene, reagent which is specific for the HMG1 gene, and reagent which is specific for the IL-1β gene, and the expression of at least three target genes selected from: TGFβ, HMG1 and IL-1β is determined in step c) of the method according to the invention.

According to another preferred embodiment of the invention, at least four specific reagents which are selected from the following specific reagents are made available in step b) of the method according to the invention: reagent which is specific for the TGFβ gene, reagent which is specific for the HMG1 gene, reagent which is specific for the IL-1β gene, and reagent which is specific for the IL-10 gene, and the expression of at least four target genes selected from: TGFβ, HMG1, IL-1β and IL-10 is determined in step c) of the method according to the invention.

According to another preferred embodiment of the invention, at least five specific reagents which are selected from the following specific reagents are made available in step b) of the method according to the invention: reagent which is specific for the TGFβ gene, reagent which is specific for the HMG1 gene, reagent which is specific for the IL-1β gene, reagent which is specific for the IL-10 gene, and reagent which is specific for the T-bet gene, and the expression of at least five target genes selected from: TGFβ, HMG1, IL-1β, IL-10 and T-bet is determined in step c) of the method according to the invention.

BRIEF DESCRIPTION OF THE DRAWING

The attached FIGURE is given as an explanatory example and is in no way limiting. It will enable the invention to be better understood.

Figure 1:
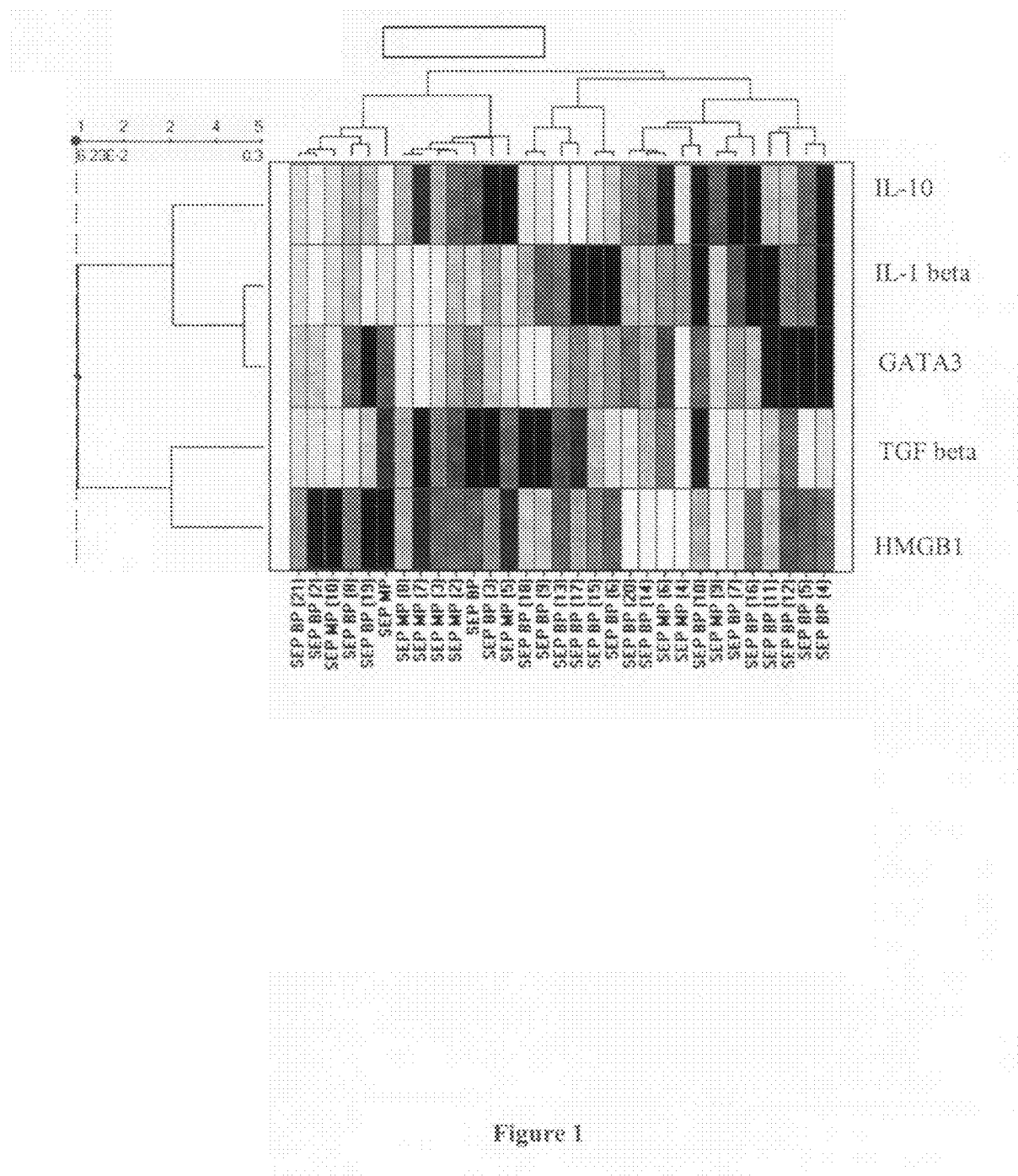
FIG. 1 shows a dendogram which was obtained from 31 samples derived from patients suffering from good-prognosis septic syndrome (GP-SEP) or poor-prognosis septic syndrome (PP-SEP) and the use of a panel of probes making it possible to analyze the expression of 5 target genes according to the invention (IL10, IL-1β, GATA-3, TGF-β and HMG1).

The following examples are given by way of illustration and are in no way limiting. They will enable the invention to be better understood.

EXAMPLE 1

Study of the Expression of the IL-10, TGFβ, HMG1, T-bet, IL-1β, TNFα and GATA-3 Genes for Diagnosing a Septic Syndrome The study was carried out on 42 patients who had developed a septic syndrome and were admitted to the Surgical or Medical intensive care unit of the Lyon-Sud hospital. Fifteen healthy volunteers were also used in order to compare the expression of the IL-10, TGFβ, HMG1, T-bet, IL-1β, TNFα and GATA-3 genes in the peripheral blood of healthy patients and of patients suffering from septic syndrome. A group of 15 healthy patients (H) was therefore distinguished from a group of 42 patients who were developing a septic syndrome (SEP).

Extracting the RNA and synthesizing the cDNA—In the case of each patient, the biological sample was a blood sample, which was taken regularly during the first 11 days following the onset of the septic syndrome which was developed by the SEP patients. Blood samples were also taken in accordance with the same protocol from the healthy patients (H). These blood samples were collected directly into PAX-Gene™ Blood RNA tubes (PreAnalytix, Frankin Lakes, USA).

After the step of taking the blood sample, and in order to obtain total lysis of the cells, the tubes were left at ambient temperature for 4 h and then stored at −20° C. until the biological material was extracted. More precisely, in this protocol, the total RNA was extracted using the PAXGene Blood RNA® (PreAnalytix) kits while observing the manufacturer's recommendations. In brief, the tubes were centrifuged (10 min, 3000 g) in order to obtain a nucleic acid pellet. This pellet was washed and taken up in buffer containing the proteinase K which was required for digesting the proteins (10 min at 55° C.). A new centrifugation (5 min, 19 000 g) was carried out in order to remove the cell debris and ethanol was added in order to optimize the conditions for fixing the nucleic acids. The total RNA was fixed specifically on PAXgene RNA spin columns and, before it was eluted, the contaminating DNA was digested using the RNAse-free DNAse set (Qiagen Ltd, Crawley, UK).

In the case of each extraction, the quality of the total RNA was verified by agarose gel electrophoresis and staining with ethidium bromide. A reverse transcription (RT) reaction was carried out in a final volume of 20 µl. The total RNA (1 µg) was mixed with 1 µl of 50 µM polyT and 1 µl of dNTP mix (ThermoScript™ RT-PCR system, Invitrogen), and the whole was incubated at 65° C. for 5 min. After cooling in ice, the solution was mixed with 4 µl of 5×cDNA synthesis buffer, 1 µl of RNAse out (40 U/µl), 1 µL of DEPC-treated water and 1 µl of Thermoscript RT (15 U/µl), all of which products were derived from the ThermoScript™ RT-PCR system (Invitrogen). The reverse transcription was carried out at 50° C. for 1 h and then stopped by incubating at 85° C. for 5 min. In order to conclude, each solution of cDNA was diluted 1/10 in the DEPC water.

Preparing standards for generating quantification ranges— The HMG1 standard was prepared by a PCR (polymerase chain reaction) amplification which was taken to saturation. The amplicons which were obtained were purified (PCR purification kit, Qiagen Ltd) and the presence of one unique amplicon was verified by agarose gel electrophoresis and staining with ethidium bromide.

The standards of the "housekeeping" gene cyclophilin B and of the target genes TGFβ, IL-1β, T-bet, GATA3 and IL-10 were obtained from Search-LC (Heidelberg, Germany).

Analyzing the expression of the mRNAs by means of real time PCR—The mRNAs of the target genes TGFβ, IL-1β, T-bet, GATA3, IL-10 and TNFα were quantified by means of real time quantitative PCR using the LightCycler™ (Roche). The PCR reactions were carried out using the Fast-Start™ DNA Master SYBR Green I real-time PCR kit (Roche Molecular Biochemicals). Each PCR was carried out in a final volume of 20 µl containing 1 µl of LC-Fast Start Reaction Mix SYBR Green I, 1 µl of LC-Fast Start DNA Master SYBR Green I/Enzyme (including Taq DNA polymerase, the reaction buffer and a mixture of deoxynucleotide triphosphates), $MgCl_2$ (final concentration 3 mM), the sense and antisense primers (final concentration 0.5 µM, each obtained from Search-LC—Heidelberg, Germany), and 10 µl of cDNA solution. After a step of denaturation at 95° C. for 10 min, the amplification was carried out by means of 40 cycles of a "touch-down" PCR protocol (10 s at 95° C. and 10 s of hybridization at 68-58° C., followed by an extension of 16 s at 72° C.). The fluorescence emitted by the SYBR Green was measured at the end of each cycle.

In order to confirm the specificity of the amplification, the PCR products were systematically subjected to a fusion curve analysis (LightCycler™—Roche). For this, the PCR products were treated with a temperature which ascended from 58 to 98° C. with a rate of increase of 0.1° C./s. In the case of each PCR product, a single peak was obtained when the curve was analyzed with this peak being characterized by a specific fusion temperature.

The combination of primers employed for quantifying HMG1 is that described by Sotiriou et al (Breast Cancer Res. 2002, 4:1-8 corresponding to the sense primer: 5'-GCG GAC AAG GCC CGT TA-3' (SEQ ID NO:1); and antisense primer: 5'-AGA GGA AGA AGG CCG AAG GA-3' (SEQ ID NO:2) (PCR product: 119 bp).

The primer combinations which were required for quantifying the housekeeping gene cyclophilin B and the target genes TGFb, IL-1b, T-bet, GATA3 and IL-10 were obtained from Search-LC (Heidelberg, Germany). Thus, in the case of the housekeeping gene cyclophilin B, the Genbank accession No. was M60857 and the 105-338 region was amplified. In the case of IL-1b, the Genbank accession No. was M15330 and the 438-642 region was amplified. In the case of TNFα, the Genbank accession No. was X01394 and the 373-783 region was amplified. In the case of T-bet, the Genbank accession No. was AF241243 and the 461-669 region was amplified. In the case of GATA3, the Genbank accession No. was X55037 and the 1023-1294 region was amplified. In the case of TGF-b1, the Genbank accession No. was X02812 and the 1540-1818 region was amplified. In the case of IL-10 the Genbank accession No. was AY029171 and the 126-413 region was amplified.

The quantity of target mRNA relative to the quantity of mRNA of the housekeeping gene cyclophilin B was analyzed by the relative quantification technique using the LightCycler Relative Quantification Software (Roche Molecular Biochemicals). The "Second Derivative Maximum Method" of the LightCycler™ (Roche) software package was used for automatically determining the crossing point (Cp) for each sample. The value of the Cp was defined as being the number of cycles for which the fluorescence was significantly different from the background.

In the case of each standard, five dilutions in a 1/10 series were prepared in quadruplicate in order to generate a calibration curve which expressed the Cp as a function of the logarithm of the number of copies. The standard dilutions were optimized so as to ensure that the calibration curve covered the level of expression which was expected for the target gene and for the housekeeping gene. The relative standard curves describing the efficacy of the PCR for the target gene and the housekeeping gene were generated and employed for performing a quantification using the LightCycler Relative Quantification Software (Roche Molecular Biochemicals).

Results Obtained

The results which were obtained are presented in table 1 below.

TABLE 1

|  | H patients | SEP patients | p |
|---|---|---|---|
| IL-10 | 0.0020 ± 0.0002 | 0.0259 ± 0.0048 | <0.001 |
| TNFα | 0.0176 ± 0.0025 | 0.0817 ± 0.0150 | <0.001 |
| IL-1β | 0.8121 ± 0.0544 | 1.0114 ± 0.2110 | 0.43 |
| HMG1 | 0.9736 ± 0.0656 | 1.4807 ± 0.0815 | <0.001 |
| GATA3 | 0.0329 ± 0.0026 | 0.0077 ± 0.0010 | <0.001 |
| T-bet | 0.0002 ± 0.0001 | 0.0051 ± 0.0010 | <0.001 |
| TGFβ | 0.5835 ± 0.0607 | 0.2759 ± 0.0200 | <0.001 |

This table 1 records the levels of expression of the IL-10, IL-1β, TNFα, HMG1, GATA3, TGFβ and T-bet mRNAs in 15 healthy patients (H) and 42 patients who were developing a septic syndrome (SEP), with the results for the latter being obtained from samples of total blood which were collected during the course of the first three days following the onset of the septic syndrome. The comparison between the H and SEP patient groups was performed using the Mann Whitney nonparametric U test, and the probability value (p) was calculated. The results are expressed by the relative quantification ratio between the mRNA of the target gene and the mRNA of the housekeeping gene cyclophilin B. The results are expressed by the mean of the ratios obtained for each of the patient groups. The SEM (standard error of the mean) was also calculated for each of the groups. The values given in table 1 are the means obtained ± the SEM. The values were regarded as being statistically different when the value obtained for p was less than 0.05.

The SEP patients exhibited a level of expression of the IL-10 and TNFα mRNAs which was significantly increased as compared with the healthy volunteers H (+10% and +4%, respectively). Surprisingly, the inventors also demonstrated an overexpression of the HMG1 mRNA in the SEP patients (+50%). In addition, the inventors also demonstrated that the level of expression of the T-bet mRNA was significantly increased as compared with the healthy volunteers H (+24%). Conversely, the expression of the GATA3 mRNA was significantly decreased in the SEP patients as compared with the healthy volunteers H (−70%).

Conclusion—Studying the expression of the mRNAs of the genes encoding T-bet and GATA3, as well as HMG1, on the basis of whole blood samples thus makes it possible to diagnose a patient who is developing a septic syndrome.

EXAMPLE 2

Using RT PCR to Analyze the Expression of the IL-10, TGFβ, HMG1, T-bet, IL-1β, TNFα and GATA-3 Genes for the Purpose of Predicting a Septic Syndrome Subsequently, the inventors looked for a tool for predicting a septic syndrome during the first 72 h following the onset of a septic shock.

For this, a study was carried out on 42 SEP patients who were developing a septic syndrome and had been admitted to the surgical or medical intensive care unit of the Lyon-Sud hospital. More precisely, these patients suffering from a septic syndrome were selected during the first 72 h following the onset of a septic shock in accordance with the inclusion criteria, as previously defined, specified by the American College of Chest Physicians/Society of Critical Care Medicine. Each patient was followed for a maximum period of 28 days. A distinction was then made between a group of 26 patients who were developing a good-prognosis septic syndrome (GP-SEP) and a group of 16 patients who were developing a poor-prognosis septic syndrome (PP-SEP).

Extracting the RNA and synthesizing the cDNA—This step was carried out in accordance with the protocol which was previously described in example 1.

Preparing the standards for generating the quantification ranges—This step was carried out in accordance with the protocol which was previously described in example 1.

Analyzing the expression of the mRNAs by means of real-time PCR—This step was carried out in accordance with the protocol which was previously described in example 1.

Results Obtained

The results which were obtained are presented in table 2 below.

TABLE 2

|  | PP-SEP patients | GP-SEP patients | p |
|---|---|---|---|
| IL-10 | 0.042 ± 0.010 | 0.016 ± 0.003 | 0.1 |
| TNFα | 0.103 ± 0.028 | 0.069 ± 0.017 | 0.22 |
| IL-1β | 1.147 ± 0.530 | 0.928 ± 0.117 | 0.14 |
| HMG1 | 1.809 ± 0.142 | 1.278 ± 0.077 | 0.01 |
| GATA3 | 0.006 ± 0.001 | 0.009 ± 0.001 | 0.25 |
| T-bet | 0.003 ± 0.001 | 0.006 ± 0.001 | 0.18 |
| TGFβ | 0.244 ± 0.022 | 0.296 ± 0.033 | 0.28 |

This table records the levels of expression of the IL-10, IL-1β, TNFα, HMG1, GATA3, TGFβ and T-bet mRNAs in the good-prognosis patients (GP-SEP) and poor-prognosis patients (PP-SEP), which levels of expression were obtained on the basis of whole blood samples which were taken during the course of the first three days following the onset of the septic shock. The comparison between the good-prognosis and poor-prognosis patient groups was performed using the Mann Whitney nonparametric U test, and the probability value (p) was calculated. The results are expressed by the relative quantification ratio between the mRNA of the target gene and the mRNA of the housekeeping gene cyclophilin B. The results are expressed by the mean of the ratios obtained for each of the patient groups. The SEM (standard error of the mean) was also calculated for each of the groups. The values given in table 2 are the means obtained±the SEM. The values were regarded as being statistically different when the value obtained for p was less than 0.05. The poor-prognosis patients exhibited a level of expression of the IL-10, TNFα and HMG1 mRNAs which was increased as compared with the good-prognosis patients. The difference was statistically significant in the case of IL-10 and HMG1. Contrary to the situation with IL-10, TNFα and HMG1, the poor-prognosis patients had a tendency to exhibit levels of expression of the GATA3, T-bet, IL-1β and TGFβ mRNAs which were lower than those of the good-prognosis patients.

The inventors demonstrated that studying a profile of the expression of several genes makes it possible to obtain a tool for predicting septic syndrome and, in particular, septic shock.

For this reason, the table below presents a hierarchical clustering analysis of 36 GP-SEP and PP-SEP patients using the expression of from 2 to 5 genes which were measured during the first three days following the onset of the septic shock. The hierarchical clustering function of the Spofire software package was used for carrying out this analysis. The results which were employed for the analysis are expressed by the relative quantification ratio between the mRNA of the target gene and the mRNA of the housekeeping gene cyclophilin B. In order to take account of the constitutive expression differences between the genes, the levels of expression of each gene were normalized by calculating a reduced centered variable. Two subclusters were obtained for each of the analyses which were performed, with the one subcluster mainly grouping together poor-prognosis patients (PP-SEP) and the other subcluster grouping together good-prognosis patients (GP-SEP). For each of the 2 groups, table 3 gives the percentage of patients who were clustered together, that is to say the percentage of patients who were classified as being PP and who were in fact poor-prognosis patients and the percentage of patients who were classified as being GP and who were in fact good-prognosis patients.

TABLE 3

| Analyzed genes | % of properly classified PP-SEP patients | % of properly classified GP-SEP patients |
| --- | --- | --- |
| TGFβ, HMG1 | 82 | 68 |
| TGFβ, IL-1β, HMG1 | 82 | 72 |
| IL-10, TGFβ, IL-1β, HMG1 | 82 | 80 |
| IL-10, TGFβ, IL-1β, HMG1, T-bet | 82 | 80 |

These results show that simultaneously studying the expression of 2 genes selected from IL-10, TGFβ, IL-1β, HMG1, T-bet, TNFα and GATA3, in particular TGFβ and HMG1, makes it possible to properly classify more than 80% of the PP-SEP patients. Comparable results were obtained when simultaneously studying the expression of 3 genes selected from IL-10, TGFβ, IL-1β, HMG1, T-bet, TNFα and GATA3, in particular TGFβ, IL-1β and HMG1, when simultaneously studying the expression of 4 genes selected from IL-10, TGFβ, IL-1β, HMG1, T-bet, TNFα and GATA3, in particular TGFβ, IL-1β, IL-10 and HMG1, and when simultaneously studying the expression of 5 genes selected from IL-10, TGFβ, IL-1β, HMG1, T-bet, TNFα and GATA3, in particular TGFβ, IL-1β, IL-10, T-bet and HMG1.

Conclusion—Analyzing the expression profile of at least two genes selected from IL-10, TGFβ, IL-1β, HMG1, T-bet, TNFα and GATA3 on the basis of whole blood samples thus makes possible an early prediction of the survival of patients who are presenting a septic syndrome and who are developing, in particular, a septic shock. More specifically, analyzing the expression of a panel of genes comprising at least IL-10, IL1-β, TGF-β and HMG-1 makes it possible to very efficiently discriminate between good-prognosis patients and poor-prognosis patients. This can enable an intensive care physician to rapidly identify the poor-prognosis patients and therefore direct the care of the patients towards using powerful and expensive treatments.

EXAMPLE 3

Analyzing, on a DNA Chip, the Expression of the IL-10, TGFβ, HMG1, T-bet, IL-1β, TNFα and GATA-3 Genes for the Purpose of Predicting a Septic Syndrome The results presented in example 2 were validated by using another technique which was applied to new patient samples. For this, a study was carried out on 31 patients who were developing a septic syndrome and who had been admitted to the surgical or medical intensive care unit of the Lyon-Sud hospital. More specifically, these patients suffering from septic syndrome were selected between the second and fourth days following the onset of a septic shock in accordance with the inclusion criteria, as previously defined, which were specified by the American College of Chest Physicians/Society of Critical Care Medicine. Each patient was followed for a maximum period of 28 days. A distinction as then made between a group of 21 patients who were developing a good-prognosis septic syndrome (GP-SEP) and a group of 10 patients who were developing a poor-prognosis septic syndrome (PP-SEP).

Extracting the RNA—This step was carried out in accordance with the protocol which was previously described in example 1.

Analyzing the expression of the mRNAs on a DNA chip—cDNA, and then double-stranded DNA, were synthesized from the RNA extracts. The double-stranded DNA was then used as the basis for an in-vitro transcription during which the cRNAs were labeled. The cRNAs were then hybridized on the chip. A scanner was used to read the fluorescence.

Results Obtained

The results which were obtained are presented in FIG. 1. It can be seen that the dendogram contains 31 columns, corresponding to the 31 patient samples, and 5 lines, corresponding to the 5 probes which were used for analyzing the expression of the 5 target genes. Since the samples, as well as the genes, had a comparable expression profile, as demonstrated by a correlation of the Pearson type, they were placed side by side. The samples were classified in accordance with the unweighted mean method (Spotfire Decision Site for Functional Genomics V7.1, manual) while the genes were classified in accordance with the mean expression value obtained in the set of samples. After using the Microarray Suite (MAS5.0, Affymetrix) software to normalize the fluorescence signals which were generated, the level of expression is represented by different levels of color. Thus, the color white corresponds to a low level of expression, while the color gray corresponds to an intermediate level of expression and the color black corresponds to a high level of expression. The length of the branches of the dendogram is correlated with the expression profile and the dotted line which divides the dendogram distinguishes two groups of patients: a first "PP-SEP" group of poor-prognosis patients and a second "GP-SEP" group of good-prognosis patients.

These results showed that simultaneously studying the expression of 5 genes selected from IL-10, TGFβ, IL-1β, HMG1, T-bet, TNFα and GATA3, in particular TGFβ, IL-1β, IL-10, GATA-3 and HMG1, enable 70% of the patients to be classified properly.

The inventors also demonstrated that studying a profile, as defined in example 2, of the expression of several genes in patients during the first 72 h following the onset of a septic shock was also applicable in the case of patients who were between the second and fourth days following the onset of a septic shock.

Conclusion—Analyzing the profile of the expression of at least two genes selected from IL-10, TGFβ, IL-1β, HMG1, T-bet, TNFα and GATA3 on the basis of whole blood samples thus makes it possible to predict the survival of patients both during the first 72 h following the onset of a septic shock and between the second and fourth days following the onset of a septic shock. More specifically, analyzing the expression of a panel of genes comprising at least IL-10, IL1-β, TGF-β and HMG-1 makes it possible to discriminate very effectively between good-prognosis patients and poor-prognosis patients, both at the very beginning of septic shock as well as several days afterwards. This can enable the intensive care physician to rapidly identify poor-prognosis patients and therefore direct the care of the patients towards using powerful and expensive treatments.

The invention claimed is:

1. A method for diagnosing and/or predicting a septic syndrome, the method comprising:
   a. obtaining a blood sample from a patient;
   b. extracting biological material from the blood sample;
   c. contacting the biological material with:
      a reagent for demonstrating expression of IL-10 gene,
      a reagent for demonstrating expression of TGFβ gene,
      a reagent for demonstrating expression of HMG1 gene,
      a reagent for demonstrating expression of IL-1β gene; and
      a reagent for demonstrating expression of T-bet gene;
   d. determining the expression levels of the IL-10 gene, TGFβ gene, the HMG1 gene, the IL-1β gene and the T-bet gene in said blood sample; and
   e. comparing the expression levels of the IL-10 gene, the TGFβ gene, the HMG1 gene, the IL-1β gene and T-bet gene in said blood sample to known control mean expression values of each of the genes in order to diagnose and/or predict a septic syndrome based on a variation in the expression of each gene in the blood sample when compared to the corresponding known control mean expression value.

2. The method of claim 1, wherein the biological material is a nucleic acid.

3. The method of claim 1, wherein:
   the reagent for demonstrating expression of the IL-10 gene comprises at least one amplification primer specific for the IL-10 gene;
   the reagent for demonstrating expression of the TGFβ gene comprises at least one amplification primer specific for the TGFβ gene;
   the reagent for demonstrating expression of the HMG1 gene comprises at least one amplification primer specific for the HMG1 gene;
   the reagent for demonstrating expression of the IL-1β gene comprises at least one amplification primer specific for the IL-1β gene; and
   the reagent for demonstrating expression of the T-bet gene comprises at least one amplification primer specific for the T-bet gene.

4. The method of claim 1, wherein:
   the reagent for demonstrating expression of the IL-10 gene comprises at least one hybridization probe specific for the IL-10 gene;
   the reagent for demonstrating expression of the TGFβ gene comprises at least one hybridization probe specific for the TGFβ gene;
   the reagent for demonstrating expression of the HMG1 gene comprises at least one hybridization probe specific for the HMG1 gene;
   the reagent for demonstrating expression of the IL-1β gene comprises at least one hybridization probe specific for the IL-1β gene; and
   the reagent for demonstrating expression of the T-bet gene comprises at least one hybridization probe specific for the T-bet gene.

* * * * *